(12) United States Patent
Lim et al.

(10) Patent No.: US 9,617,570 B2
(45) Date of Patent: Apr. 11, 2017

(54) ACID RESISTANT YEAST CELL AND USE THEREOF

(71) Applicant: Samsung Electronics Co., Ltd., Suwon-si, Gyeonggi-do (KR)

(72) Inventors: Huisub Lim, Seoul (KR); Changduk Kang, Gwacheon-si (KR); Jiyoon Song, Seoul (KR); Seunghyun Lee, Asan-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/622,315

(22) Filed: Feb. 13, 2015

(65) Prior Publication Data

US 2015/0225752 A1 Aug. 13, 2015

(30) Foreign Application Priority Data

Feb. 13, 2014 (KR) ........................ 10-2014-0016790

(51) Int. Cl.
  *C12N 1/19* (2006.01)
  *C12P 7/56* (2006.01)
  *C12N 15/01* (2006.01)
  *C12R 1/865* (2006.01)

(52) U.S. Cl.
  CPC ................ *C12P 7/56* (2013.01); *C12N 15/01* (2013.01); *C12R 1/865* (2013.01)

(58) Field of Classification Search
  None
  See application file for complete search history.

(56) References Cited

U.S. PATENT DOCUMENTS

| | | | |
|---|---|---|---|
| 8,137,953 B2 * | 3/2012 | Miller | C12N 9/0006 435/254.2 |
| 8,765,446 B2 | 7/2014 | Lee et al. | |
| 2007/0031950 A1 | 2/2007 | Winkler | |
| 2007/0161098 A1 * | 7/2007 | Yamaguchi | C12N 9/0006 435/139 |
| 2014/0051138 A1 * | 2/2014 | Na | C12P 7/56 435/139 |
| 2015/0064752 A1 * | 3/2015 | Lee | C12P 7/56 435/139 |

FOREIGN PATENT DOCUMENTS

| | | | | |
|---|---|---|---|---|
| JP | WO 2012147903 A1 * | 11/2012 | ................ | C12P 7/56 |
| WO | 2011/037414 | 3/2011 | | |

OTHER PUBLICATIONS

Lawrence, C.W., "Classical mutagenesis techniques" in Guthrie C, Fink GR (eds) Methods in Enzymology, vol. 194. Academic Press, San Diego, CA, pp. 273-281, 1991.*
Chen et al., Appl. Environ. Microbiol. doi:10.1128/AEM.03718-15, posted online Jan. 29, 2016, 39 pages.*
The Merck Index, "Ethyl Methanesulfonate", Thirteenth Edition (2001).

* cited by examiner

*Primary Examiner* — David J Steadman
(74) *Attorney, Agent, or Firm* — Leydig, Voit & Mayer, Ltd.

(57) ABSTRACT

*Saccharomyces cerevisiae* having acid resistance at a pH of about 2.0 to about 5.0, a method of preparing the *Saccharomyces cerevisiae*, and a method of producing lactate.

4 Claims, 5 Drawing Sheets

SEQUENCE LISTING

<160> NUMBER OF SEQ ID NOS: 35

<210> SEQ ID NO 1
<211> LENGTH: 563
<212> TYPE: PRT
<213> ORGANISM: Saccharomyces cerevisiae

<400> SEQUENCE: 1

```
Met Ser Glu Ile Thr Leu Gly Lys Tyr Leu Phe Glu Arg Leu Lys Gln
 1               5                  10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220
```

```
His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
            370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 2
<211> LENGTH: 591
<212> TYPE: PRT
<213> ORGANISM: Saccharomyces cerevisiae

<400> SEQUENCE: 2

Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
            20                  25                  30
```

```
Gly Ser Thr Val Pro Lys Ser Lys Ser Phe Glu Gln Asp Ser Arg Lys
            35                  40                  45
Arg Thr Gln Ser Trp Thr Ala Leu Arg Val Gly Ala Ile Leu Ala Ala
 50                  55                  60
Thr Ser Ser Val Ala Tyr Leu Asn Trp His Asn Gly Gln Ile Asp Asn
 65                  70                  75                  80
Glu Pro Lys Leu Asp Met Asn Lys Gln Lys Ile Ser Pro Ala Glu Val
                 85                  90                  95
Ala Lys His Asn Lys Pro Asp Asp Cys Trp Val Val Ile Asn Gly Tyr
                100                 105                 110
Val Tyr Asp Leu Thr Arg Phe Leu Pro Asn His Pro Gly Gly Gln Asp
            115                 120                 125
Val Ile Lys Phe Asn Ala Gly Lys Asp Val Thr Ala Ile Phe Glu Pro
            130                 135                 140
Leu His Ala Pro Asn Val Ile Asp Lys Tyr Ile Ala Pro Glu Lys Lys
145                 150                 155                 160
Leu Gly Pro Leu Gln Gly Ser Met Pro Pro Glu Leu Val Cys Pro Pro
                165                 170                 175
Tyr Ala Pro Gly Glu Thr Lys Glu Asp Ile Ala Arg Lys Glu Gln Leu
            180                 185                 190
Lys Ser Leu Leu Pro Pro Leu Asp Asn Ile Ile Asn Leu Tyr Asp Phe
            195                 200                 205
Glu Tyr Leu Ala Ser Gln Thr Leu Thr Lys Gln Ala Trp Ala Tyr Tyr
            210                 215                 220
Ser Ser Gly Ala Asn Asp Glu Val Thr His Arg Glu Asn His Asn Ala
225                 230                 235                 240
Tyr His Arg Ile Phe Phe Lys Pro Lys Ile Leu Val Asp Val Arg Lys
                245                 250                 255
Val Asp Ile Ser Thr Asp Met Leu Gly Ser His Val Asp Val Pro Phe
            260                 265                 270
Tyr Val Ser Ala Thr Ala Leu Cys Lys Leu Gly Asn Pro Leu Glu Gly
            275                 280                 285
Glu Lys Asp Val Ala Arg Gly Cys Gly Gln Gly Val Thr Lys Val Pro
            290                 295                 300
Gln Met Ile Ser Thr Leu Ala Ser Cys Ser Pro Glu Glu Ile Ile Glu
305                 310                 315                 320
Ala Ala Pro Ser Asp Lys Gln Ile Gln Trp Tyr Gln Leu Tyr Val Asn
                325                 330                 335
Ser Asp Arg Lys Ile Thr Asp Asp Leu Val Lys Asn Val Glu Lys Leu
            340                 345                 350
Gly Val Lys Ala Leu Phe Val Thr Val Asp Ala Pro Ser Leu Gly Gln
            355                 360                 365
Arg Glu Lys Asp Met Lys Leu Lys Phe Ser Asn Thr Lys Ala Gly Pro
            370                 375                 380
Lys Ala Met Lys Lys Thr Asn Val Glu Glu Ser Gln Gly Ala Ser Arg
385                 390                 395                 400
Ala Leu Ser Lys Phe Ile Asp Pro Ser Leu Thr Trp Lys Asp Ile Glu
                405                 410                 415
Glu Leu Lys Lys Lys Thr Lys Leu Pro Ile Val Ile Lys Gly Val Gln
            420                 425                 430
Arg Thr Glu Asp Val Ile Lys Ala Ala Glu Ile Gly Val Ser Gly Val
            435                 440                 445
```

```
Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Val Arg Arg Gly Thr
                485                 490                 495

Asp Val Leu Lys Ala Leu Cys Leu Gly Ala Lys Gly Val Gly Leu Gly
                500                 505                 510

Arg Pro Phe Leu Tyr Ala Asn Ser Cys Tyr Gly Arg Asn Gly Val Glu
            515                 520                 525

Lys Ala Ile Glu Ile Leu Arg Asp Glu Ile Glu Met Ser Met Arg Leu
530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
                580                 585                 590

<210> SEQ ID NO 3
<211> LENGTH: 391
<212> TYPE: PRT
<213> ORGANISM: Saccharomyces cerevisiae

<400> SEQUENCE: 3

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
                20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240
```

```
Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 4
<211> LENGTH: 1692
<212> TYPE: DNA
<213> ORGANISM: Saccharomyces cerevisiae

<400> SEQUENCE: 4
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact gaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcacccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca gaacattgt cgaattccac tccgaccaca tgaagatcag aaacgccact     960
ttcccaggtg tccaaatgaa attcgttttg caaaagttgt tgaccactat tgctgacgcc    1020
gctaagggtt acaagccagt tgctgtccca gctagaactc cagctaacgc tgctgtccca    1080
gcttctaccc cattgaagca agaatggatg tggaaccaat gggtaactt cttgcaagaa    1140
ggtgatgttg tcattgctga aaccggtacc tccgctttcg gtatcaacca aaccactttc    1200
```

-continued

| | |
|---|---:|
| ccaaacaaca cctacggtat ctctcaagtc ttatggggtt ccattggttt caccactggt | 1260 |
| gctaccttgg gtgctgcttt cgctgctgaa gaaattgatc caaagaagag agttatctta | 1320 |
| ttcattggtg acggttcttt gcaattgact gttcaagaaa tctccaccat gatcagatgg | 1380 |
| ggcttgaagc catacttgtt cgtcttgaac aacgatggtt acaccattga aaagttgatt | 1440 |
| cacggtccaa aggctcaata acgaaattc aaggttggg accacctatc cttgttgcca | 1500 |
| actttcggtg ctaaggacta tgaaacccac agagtcgcta ccaccggtga atgggacaag | 1560 |
| ttgacccaag acaagtcttt caacgacaac tctaagatca gaatgattga aatcatgttg | 1620 |
| ccagtcttcg atgctccaca aaacttggtt gaacaagcta agttgactgc tgctaccaac | 1680 |
| gctaagcaat aa | 1692 |

<210> SEQ ID NO 5
<211> LENGTH: 1776
<212> TYPE: DNA
<213> ORGANISM: Saccharomyces cerevisiae

<400> SEQUENCE: 5

| | |
|---|---:|
| atgctaaaat acaaaccttt actaaaaatc tcgaagaact gtgaggctgc tatcctcaga | 60 |
| gcgtctaaga ctagattgaa cacaatccgc gcgtacggtt ctaccgttcc aaaatccaag | 120 |
| tcgttcgaac aagactcaag aaaacgcaca cagtcatgga ctgccttgag agtcggtgca | 180 |
| attctagccg ctactagttc cgtggcgtat ctaaactggc ataatggcca aatagacaac | 240 |
| gagccgaaac tggatatgaa taaacaaaag atttcgcccg ctgaagttgc caagcataac | 300 |
| aagcccgatg attgttgggt tgtgatcaat ggttacgtat acgacttaac gcgattccta | 360 |
| ccaaatcatc caggtgggca ggatgttatc aagtttaacg ccgggaaaga tgtcactgct | 420 |
| atttttgaac cactacatgc tcctaatgtc atcgataagt atatagctcc cgagaaaaaa | 480 |
| ttgggtcccc ttcaaggatc catgcctcct gaacttgtct gtcctcctta tgctcctggt | 540 |
| gaaactaagg aagatatcgc tagaaaagaa caactaaaat cgctgctacc tcctctagat | 600 |
| aatattatta acctttacga ctttgaatac ttggcctctc aaactttgac taaacaagcg | 660 |
| tgggcctact attcctccgg tgctaacgac gaagttactc acagagaaaa ccataatgct | 720 |
| tatcatagga ttttttcaa accaaagatc cttgtagatg tacgcaaagt agacatttca | 780 |
| actgacatgt tgggttctca tgtggatgtt cccttctacg tgtctgctac agctttgtgt | 840 |
| aaactgggaa acccctaga aggtgaaaaa gatgtcgcca gaggttgtgg ccaaggtgtg | 900 |
| acaaaagtcc cacaaatgat atctactttg gcttcatgtt cccctgagga aattattgaa | 960 |
| gcagcaccct ctgataaaca aattcaatgg taccaactat atgttaactc tgatagaaag | 1020 |
| atcactgatg atttggttaa aaatgtgaaa aagctgggtg taaaggcatt atttgtcact | 1080 |
| gtggatgctc caagtttagg tcaaagagaa aaagatatga agctgaaatt ttccaataca | 1140 |
| aaggctggtc caaaagcgat gaagaaaact aatgtagaag aatctcaagg tgcttcgaga | 1200 |
| gcgttatcaa agtttattga ccccctcttt g acttggaaag atatagaaga gttgaagaaa | 1260 |
| aagacaaaac tacctattgt tatcaaaggt gttcaacgta ccgaagatgt tatcaaagca | 1320 |
| gcagaaatcg gtaagtgg ggtggttcta tccaatcatg gtggtagaca attagatttt | 1380 |
| tcaagggctc ccattgaagt cctggctgaa accatgccaa tcctggaaca acgtaacttg | 1440 |
| aaggataagt tggaagtttt cgtggacggt ggtgttcgtc gtggtacaga tgtcttgaaa | 1500 |
| gcgttatgtc taggtgctaa aggtgttggt ttgggtagac cattcttgta tgcgaactca | 1560 |
| tgctatggtc gtaatggtgt tgaaaaagcc attgaaattt taagagatga aattgaaatg | 1620 |

```
tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776
```

<210> SEQ ID NO 6
<211> LENGTH: 1176
<212> TYPE: DNA
<213> ORGANISM: Saccharomyces cerevisiae

<400> SEQUENCE: 6

```
atgtctgctg ctgctgatag attaaactta acttccggcc acttgaatgc tggtagaaag     60
agaagttcct cttctgtttc tttgaaggct gccgaaaagc ctttcaaggt tactgtgatt    120
ggatctggta actggggtac tactattgcc aaggtggttg ccgaaaattg taagggatac    180
ccagaagttt tcgctccaat agtacaaatg tgggtgttcg aagaagagat caatggtgaa    240
aaattgactg aaatcataaa tactagacat caaaacgtga atacttgcc tggcatcact     300 ctacccgaca atttggttgc taatccagac ttgattgatt cagtcaagga tgtcgacatc    360
atcgttttca acattccaca tcaattttg ccccgtatct gtagccaatt gaaaggtcat     420
gttgattcac acgtcagagc tatctcctgt ctaaagggtt ttgaagttgg tgctaaaggt    480
gtccaattgc tatcctctta catcactgag gaactaggta ttcaatgtgg tgctctatct    540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atggccaatc cgctcaaggt   1020
ttaattacct gcaagaaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                              1176
```

<210> SEQ ID NO 7
<211> LENGTH: 332
<212> TYPE: PRT
<213> ORGANISM: Pelodiscus sinensis japonicus

<400> SEQUENCE: 7

```
Met Ser Val Lys Glu Leu Leu Ile Gln Asn Val His Lys Glu Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Arg Gly Glu Met Leu Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
```

```
            85                  90                  95
Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Asp Cys Met Leu Leu Val Val Ser Asn Pro Val Asp Ile Leu Thr
130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
            165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
            195                 200                 205

Val Ser Leu Lys Ala Leu Tyr Pro Asp Leu Gly Thr Asp Ala Asp Lys
            210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
            245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
            275                 280                 285

Leu Ser Val Pro Cys Val Leu Gly Tyr Ala Gly Ile Thr Asp Val Val
            290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
            325                 330

<210> SEQ ID NO 8
<211> LENGTH: 332
<212> TYPE: PRT
<213> ORGANISM: Ornithorhynchus anatinus

<400> SEQUENCE: 8

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
            50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
            85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125
```

```
Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
                180                 185                 190

His Gly Asp Ser Ser Val Pro Val Trp Ser Gly Val Asn Val Ala Gly
                195                 200                 205

Val Ser Leu Lys Asn Leu His Pro Asp Leu Gly Thr Asp Ala Asp Lys
210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
                260                 265                 270

Ile Ser Thr Met Ile Lys Gly Leu Tyr Gly Ile Lys Asp Glu Val Phe
                275                 280                 285

Leu Ser Val Pro Cys Val Leu Gly Gln Asn Gly Ile Ser Asp Val Val
                290                 295                 300

Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 9
<211> LENGTH: 332
<212> TYPE: PRT
<213> ORGANISM: Tursiops truncatus

<400> SEQUENCE: 9

Met Ala Thr Val Lys Asp Gln Leu Ile Gln Asn Leu Leu Lys Glu Glu
1               5                   10                  15

His Val Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175
```

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
            195                 200                 205

Val Ser Leu Lys Asn Leu His Pro Glu Leu Gly Thr Asp Ala Asp Lys
210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
            245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
            290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
            325                 330

<210> SEQ ID NO 10
<211> LENGTH: 332
<212> TYPE: PRT
<213> ORGANISM: Rattus norvegicus

<400> SEQUENCE: 10

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
        50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Gln Cys Lys Leu Leu Ile Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
            195                 200                 205

Val Ser Leu Lys Ser Leu Asn Pro Gln Leu Gly Thr Asp Ala Asp Lys

```
                    210              215                  220
Glu Gln Trp Lys Asp Val His Lys Gln Val Val Asp Ser Ala Tyr Glu
225                 230                  235                 240

Val Ile Lys Leu Lys Gly Tyr Thr Ser Trp Ala Ile Gly Leu Ser Val
                245                  250                 255

Ala Asp Leu Ala Glu Ser Ile Met Lys Asn Leu Arg Arg Val His Pro
                260                  265                 270

Ile Ser Thr Met Ile Lys Gly Leu Tyr Gly Ile Lys Glu Asp Val Phe
            275                  280                 285

Leu Ser Val Pro Cys Ile Leu Gly Gln Asn Gly Ile Ser Asp Val Val
                290                  295                 300

Lys Val Thr Leu Thr Pro Asp Glu Glu Ala Arg Leu Lys Lys Ser Ala
305                 310                  315                 320

Asp Thr Leu Trp Gly Ile Gln Lys Glu Leu Gln Phe
                325                  330
```

<210> SEQ ID NO 11
<211> LENGTH: 999
<212> TYPE: DNA
<213> ORGANISM: Pelodiscus sinensis japonicus

<400> SEQUENCE: 11

```
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccgact gcatgttgc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tgggagaaaa attaggtatt     540
cactccttat cttgtcatgg ctggataata ggcgaacatg gtgattcttc ggtacctgtt     600
tggtccgggg ttaatgtggc tggtgttagt ttaaaagcat tatatcctga cctgggtact     660
gatgccgata agaacattg gaaagaagtg cacaaacaag tggttgattc tgcttacgaa      720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900
acagacgtcg tgaagatgac attgaaatca gaggaagagg aaaaactaag aaagtcagcc     960
gatactctgt ggggcattca aaaggaattg cagtttttaa                           999
```

<210> SEQ ID NO 12
<211> LENGTH: 1267
<212> TYPE: DNA
<213> ORGANISM: Artificial Sequence
<220> FEATURE:
<223> OTHER INFORMATION: Synthetic ARS/CEN

<400> SEQUENCE: 12

```
gagctccttt catttctgat aaagtaagaa ttactccatt tatcttttca ccaacatatt      60
catagttgaa agttatcctt ctaagtacgt atacaatatt aattaaacgt aaaaacaaaa     120
```

```
ctgactgtaa aaatgtgtaa aaaaaaaata tcaaattcat agcagtttca aggaatgaaa      180
actattatga tctggtcacg tgtatataaa ttattaattt taaacccata taatttatta      240
tttttttatt ctaaagttta aagtaatttt agtagtattt tatattttga ataaatatac      300
tttaaatttt tatttttata ttttattact tttaaaaata atgttttat ttaaaacaaa       360 attataagtt aaaaagttgt tccgaaagta aaatatattt tatagttttt acaaaaataa      420
attattttta acgtattttt tttaattata tttttgtatg tgattatatc cacaggtatt      480
atgctgaatt tagctgtttc agtttaccag tgtgatagta tgattttttt tgcctctcaa      540
aagctatttt tttagaagct tcgtcttaga aataggtggt gtataaattg cggttgactt      600
ttaactatat atcattttcg atttatttat tacatagaga ggtgcttta attttttaat       660 tttattttc aataatttta aaagtgggta cttttaaatt ggaacaaagt gaaaaatatc       720
tgttatacgt gcaactgaat tttactgacc ttaaaggact atctcaatcc tggttcagaa      780
atccttgaaa tgattgatat gttggtggat tttctctgat tttcaaacaa gaggtatttt      840
atttcatatt tattatattt tttacattta ttttatattt ttttattgtt tggaagggaa      900
agcgacaatc aaattcaaaa tatattaatt aaactgtaat acttaataag agacaaataa      960
cagccaagaa tcaaatactg gttttttaat caaaagatct ctctacatgc acccaaattc     1020
attatttaaa tttactatac tacagacaga atatacgaac ccagattaag tagtcagacg     1080
cttttccgct ttattgagta tatagcctta catattttct gcccataatt tctggattta     1140
aaataaacaa aaatggttac tttgtagtta tgaaaaaagg cttttccaaa atgcgaaata     1200
cgtgttattt aaggttaatc aacaaaacgc atatccatat gggtagttgg acaaaacttc     1260
aatcgat                                                              1267
```

<210> SEQ ID NO 13
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 13

```
atttggcgag cgttggttgg tggatcaagc ccacgcgtag gcaatcctcg agcagatccg       60
ccaggcgtgt atatatagcg tggatggcca ggcaacttta gtgctgacac atacaggcat      120
atatatatgt gtgcgacgac acatgatcat atggcatgca tgtgctctgt atgtatataa      180
aactcttgtt ttcttctttt ctctaaatat tctttcctta tacattagga cctttgcagc      240
ataaattact atacttctat agacacgcaa acacaaatac acacactaa                  289
```

<210> SEQ ID NO 14
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 14

```
atagcttcaa aatgtttcta ctccttttt actcttccag attttctcgg actccgcgca       60
tcgccgtacc acttcaaaac acccaagcac agcatactaa atttcccctc tttcttcctc      120
tagggtgtcg ttaattaccc gtactaaagg tttggaaaag aaaaagaga ccgcctcgtt       180 tctttttctt cgtcgaaaaa ggcaataaaa atttttatca cgtttctttt tcttgaaaat     240 ttttttttg attttttttct ctttcgatga cctcccattg atatttaagt taataaacgg     300
```

```
tcttcaattt ctcaagtttc agtttcattt ttcttgttct attacaactt tttttacttc    360
ttgctcatta gaaagaaagc atagcaatct aatctaagtt t                        401

<210> SEQ ID NO 15
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 15
agtttatcat tatcaatact cgccatttca aagaatacgt aaataattaa tagtagtgat     60
tttcctaact ttatttagtc aaaaaattag ccttttaatt ctgctgtaac ccgtacatgc    120
ccaaaatagg gggcgggtta cacagaatat ataacatcgt aggtgtctgg gtgaacagtt    180
tattcctggc atccactaaa tataatggag cccgcttttt aagctggcat ccagaaaaaa    240
aaagaatccc agcaccaaaa tattgttttc ttcaccaacc atcagttcat aggtccattc    300
tcttagcgca actacagaga acaggggcac aaacaggcaa aaacgggca  aacctcaat    360 ggagtgatgc aacctgcctg gagtaaatga tgacacaagg caattgaccc acgcatgtat    420
ctatctcatt tcttacacc ttctattacc ttctgctctc tctgatttgg aaaaagctga    480 aaaaaaggt tgaaaccagt tccctgaaat tattccccta cttgactaat aagtatataa    540
agacggtagg tattgattgt aattctgtaa atctatttct taaacttctt aaattctact    600
tttatagtta gtcttttttt tagttttaaa acaccagaac ttagtttcga cggat         655

<210> SEQ ID NO 16
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 16
gccgggatcg aagaaatgat ggtaaatgaa ataggaaatc aaggagcatg aaggcaaaag     60
acaaatataa gggtcgaacg aaaaataaag tgaaaagtgt tgatatgatg tatttggctt    120
tgcggcgccg aaaaaacgag tttacgcaat gcacaatca tgctgactct gtggcggacc    180
cgcgctcttg ccggcccggc gataacgctg gcgtgaggc tgtgcccggc ggagtttttt    240
gcgcctgcat tttccaaggt ttaccctgcg ctaaggggcg agattggaga agcaataaga    300
atgccggttg gggttgcgat gatgacgacc acgacaactg tgtcattat ttaagttgcc    360 gaaagaacct gagtgcattt gcaacatgag tatactagaa gaatgagcca agacttgcga    420
gacgcgagtt tgccggtggt gcgaacaata gagcgaccat gaccttgaag gtgagacgcg    480
cataaccgct agagtacttt gaagaggaaa cagcaatagg gttgctacca gtataaatag    540
acaggtacat acaacactgg aaatggttgt ctgtttgagt acgctttcaa ttcatttggg    600
tgtgcacttt attatgttac aatatggaag ggaactttac acttctccta tgcacatata    660
ttaattaaag tccaatgcta gtagagaagg ggggtaacac ccctccgcgc tcttttccga    720 ttttttttcta aaccgtggaa tatttcggat atccttttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
```

```
aactaatact gtagccctag acttgatagc catcatcata tcgaagtttc actacccttt    1020
ttccatttgc catctattga agtaataata ggcgcatgca acttcttttc ttttttttc     1080 ttttctctct cccccgttgt tgtctcacca tatccgcaat gacaaaaaaa tgatggaaga    1140
cactaaagga aaaaattaac gacaaagaca gcaccaacag atgtcgttgt tccagagctg    1200 atgagggggta tctcgaagca cacgaaactt tttccttcct tcattcacgc acactactct   1260
ctaatgagca acggtatacg gccttccttc cagttacttg aatttgaaat aaaaaaaagt    1320
ttgctgtctt gctatcaagt ataaatagac ctgcaattat taatctttg tttcctcgtc     1380 attgttctcg ttcccttct tccttgtttc tttttctgca caatatttca agctatacca     1440
agcatacaat caactccaag ctggccgc                                       1468

<210> SEQ ID NO 17
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 17
tcatgtaatt agttatgtca cgcttacatt cacgccctcc ccccacatcc gctctaaccg    60
aaaaggaagg agttagacaa cctgaagtct aggtccctat ttatttttt atagttatgt     120 tagtattaag aacgttattt atatttcaaa tttttctttt ttttctgtac agacgcgtgt    180
acgcatgtaa cattatactg aaaaccttgc ttgagaaggt tttgggacgc tcgaaggctt    240
taatttgcgg cc                                                        252

<210> SEQ ID NO 18
<211> LENGTH: 31
<212> TYPE: DNA
<213> ORGANISM: Artificial Sequence
<220> FEATURE:
<223> OTHER INFORMATION: Synthetic forward primer

<400> SEQUENCE: 18
cgagctcttc gcggccacct acgccgctat c                                   31

<210> SEQ ID NO 19
<211> LENGTH: 32
<212> TYPE: DNA
<213> ORGANISM: Artificial Sequence
<220> FEATURE:
<223> OTHER INFORMATION: Synthetic reverse primer

<400> SEQUENCE: 19
gctctagata ttgatatagt gtttaagcga at                                  32

<210> SEQ ID NO 20
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 20
ggatccatgt ccgtaaagga actact                                         26

<210> SEQ ID NO 21
<211> LENGTH: 34
<212> TYPE: DNA
<213> ORGANISM: Artificial Sequence
```

```
<220> FEATURE:
<223> OTHER INFORMATION: Synthetic reverse primer

<400> SEQUENCE: 21
acgcgtcgac ttaaaactgc aattcctttt gaat                          34

<210> SEQ ID NO 22
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 22
gagctcaatt aaccctcact aaaggg                                   26

<210> SEQ ID NO 23
<211> LENGTH: 26
<212> TYPE: DNA
<213> ORGANISM: Artificial Sequence
<220> FEATURE:
<223> OTHER INFORMATION: Synthetic reverse primer

<400> SEQUENCE: 23
gagctccaaa ttaaagcctt cgagcg                                   26

<210> SEQ ID NO 24
<211> LENGTH: 60
<212> TYPE: DNA
<213> ORGANISM: Artificial Sequence
<220> FEATURE:
<223> OTHER INFORMATION: Synthetic forward primer

<400> SEQUENCE: 24
aagatctacg aagttgaagg tatgagatgg gctggtaacg ccagtcacga cgttgtaaaa    60

<210> SEQ ID NO 25
<211> LENGTH: 60
<212> TYPE: DNA
<213> ORGANISM: Artificial Sequence
<220> FEATURE:
<223> OTHER INFORMATION: Synthetic reverse primer

<400> SEQUENCE: 25
gcttccttaa cttctggctt ggacaaggta ccgacgtaaa aggtttcccg actggaaagc    60

<210> SEQ ID NO 26
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 26
cgatgcgtat tttaagtggt tctctgaaca gcacaatgtc ctcgacacca ccagtcacga    60
cgttgtaaaa                                                           70

<210> SEQ ID NO 27
<211> LENGTH: 72
<212> TYPE: DNA
<213> ORGANISM: Artificial Sequence
<220> FEATURE:
<223> OTHER INFORMATION: Synthetic reverse primer

<400> SEQUENCE: 27
```

```
ggatcacccc ccactcaagt cgttgcattg ctaacatgtg gcattctgcc caaggtttcc      60
cgactggaaa gc                                                          72
```

<210> SEQ ID NO 28
<211> LENGTH: 70
<212> TYPE: DNA
<213> ORGANISM: Artificial Sequence
<220> FEATURE:
<223> OTHER INFORMATION: Synthetic forward primer

<400> SEQUENCE: 28

```
ccctatgtct ctggccgatc acgcgccatt gtccctcaga aacaaatcaa ccagtcacga      60
cgttgtaaaa                                                             70
```

<210> SEQ ID NO 29
<211> LENGTH: 70
<212> TYPE: DNA
<213> ORGANISM: Artificial Sequence
<220> FEATURE:
<223> OTHER INFORMATION: Synthetic reverse primer

<400> SEQUENCE: 29

```
tagaagcaac tgtgccgaca gcctctgaat gagtggtgtt gtaaccaccc aggtttcccg      60
actggaaagc                                                             70
```

<210> SEQ ID NO 30
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 30

```
gctcttctct accctgtcat tc                                               22
```

<210> SEQ ID NO 31
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 31

```
tagtgtacag ggtgtcgtat ct                                               22
```

<210> SEQ ID NO 32
<211> LENGTH: 26
<212> TYPE: DNA
<213> ORGANISM: Artificial Sequence
<220> FEATURE:
<223> OTHER INFORMATION: Synthetic forward primer

<400> SEQUENCE: 32

```
ggagttgaag gcaaaattag aagtga                                           26
```

<210> SEQ ID NO 33
<211> LENGTH: 26
<212> TYPE: DNA
<213> ORGANISM: Artificial Sequence
<220> FEATURE:
<223> OTHER INFORMATION: Synthetic reverse primer

<400> SEQUENCE: 33

```
attcccttc ctgcacaaca cgagat                                            26
```

```
<210> SEQ ID NO 34
<211> LENGTH: 25
<212> TYPE: DNA
<213> ORGANISM: Artificial Sequence
<220> FEATURE:
<223> OTHER INFORMATION: Synthetic forward primer

<400> SEQUENCE: 34
tcaatgagac tgttgtcctc ctact                                              25

<210> SEQ ID NO 35
<211> LENGTH: 24
<212> TYPE: DNA
<213> ORGANISM: Artificial Sequence
<220> FEATURE:
<223> OTHER INFORMATION: Synthetic reverse primer

<400> SEQUENCE: 35
tacatccttg tcgagccttg ggca                                               24
```

ACID RESISTANT YEAST CELL AND USE THEREOF

RELATED APPLICATION

This application claims the benefit of Korean Patent Application No. 10-2014-0016790, filed on Feb. 13, 2014, in the Korean Intellectual Property Office, the disclosure of which is incorporated herein in its entirety by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 41,946 bytes ASCII (Text) file named "718416_ST25.TXT," created Feb. 11, 2015.

BACKGROUND

1. Field

The present disclosure relates to acid-resistant yeast cells and a method of preparing lactate by using the acid-resistant yeast cells.

2. Description of the Related Art

Organic acids are widely used in various industries. For example, lactate is an organic acid that is widely used in various industries such as food, pharmaceuticals, chemicals, and electronics. Lactate is a low-volatile material that is colorless, odorless, and water-soluble. Lactate is non-toxic to humans, and thus, lactate is used as a flavoring agent, an acidifier, and a preservative. Lactate is also used as a source of polylactic acid (PLA) that is an environmentally friendly, biodegradable plastic known as an alternate polymeric material.

An organic acid may be dissociated into hydrogen ions and negative ions of the organic acid at an acidity higher than a pKa value of the organic acid, for example, under a neutral condition. However, organic acids such as lactic acid exist as free acids, which do not have electromagnetic force under an acidic condition that has a lower pKa than a pKa of the organic acid. The anionic form of the organic acid may not pass through a cell membrane but a free acid form of the organic acid may pass through the cell membrane. Thus, an organic acid outside the cell membrane may flow into a cell from an environment with high concentration of the organic acid, which may decrease intracellular pH. Also, the anionic form of the organic acid is disadvantageous in that a salt needs to be added thereto to separate the organic acid in a salt form. As a result, a cell lacking acid-resistance may lose activity and die under an acidic condition including one or more organic acids.

Thus, there remains a need for an acid-resistant microorganism that retains activity when exposed to acidic conditions.

SUMMARY

Provided is genetically modified *Saccharomyces cerevisiae* cell having resistance to an acid having a pH of about 2.0 to about 5.0.

Also provided is a method of preparing an acid-resistant variant strain of *Saccharomyces cerevisiae*, the method comprising treating *Saccharomyces cerevisiae* cells with a mutagen; culturing the mutagen-treated *Saccharomyces cerevisiae* yeast cells; and selecting a variant strain of cultured *Saccharomyces cerevisiae* cells having resistance to an acid having a pH of about 2.0 to about 5.0.

A method of producing lactate also is provided, which method comprises culturing the genetically modified *Saccharomyces cerevisiae* cell in a cell culture medium, whereby the cell produces cultured products comprising lactate; and retrieving lactate from cultured products.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
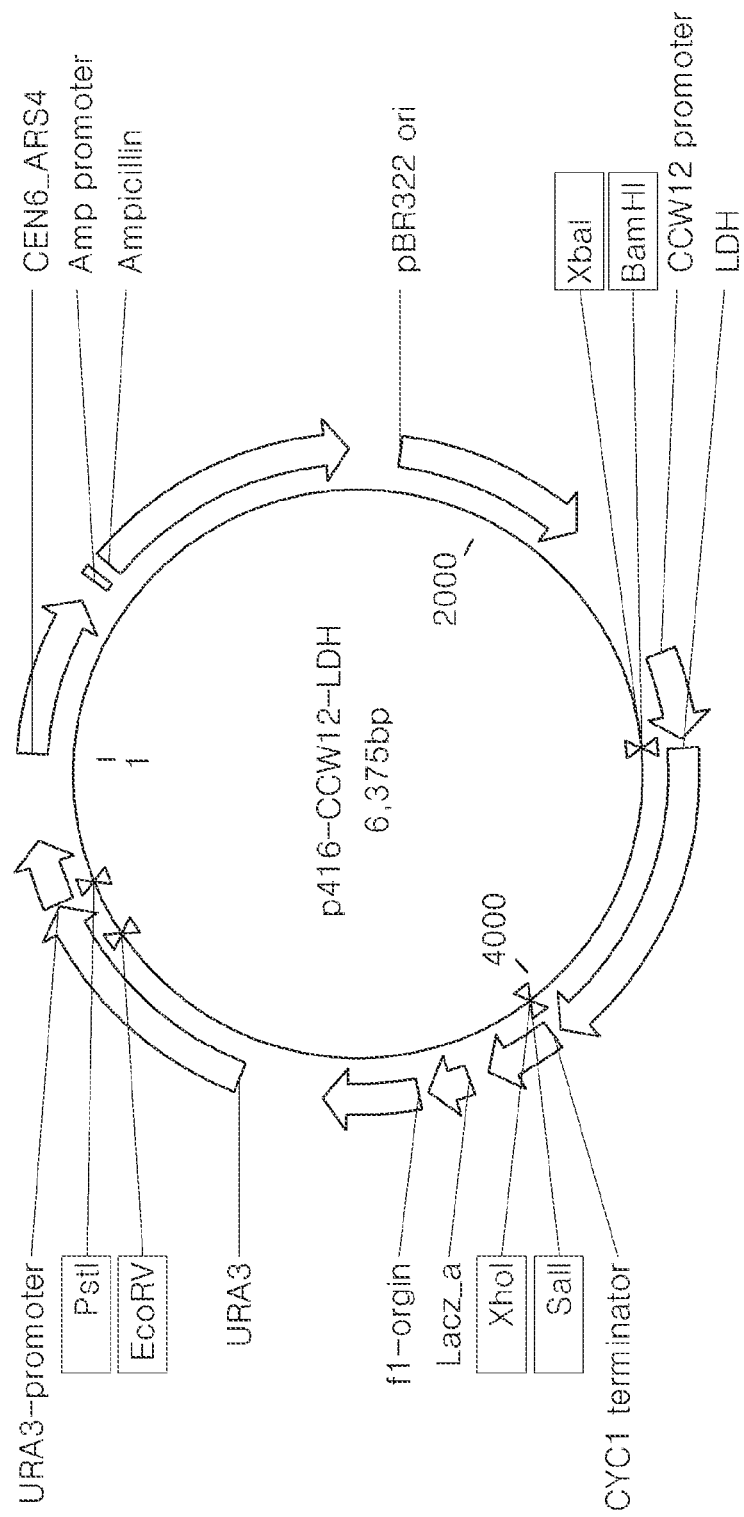
FIG. 1 is a vector map of a p416-CCW12p-LDH vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, provided is a genetically modified yeast cell comprising at least one mutation, wherein the yeast cell has acid-resistance at a pH of about 2.0 to about 5.0. In one embodiment the yeast cell is *Saccharomyces cerevisiae*.

The term "acid resistant" or "acid resistance" refers to an ability of a genetically modified yeast cell may have acid pH tolerance, i.e., may be tolerant to organic acids at low pH such as a pH of about 2.0 to about 5.0.

Also, the term "acid resistant" or "acid resistance" refers to an ability of a genetically modified yeast cell to exhibit better growth (increased rate of growth) under an acidic condition than a cell of the same type that has not been manipulated (i.e., a cell that has not been genetically modified). Also, the term "acid resistant" refers to an ability of a genetically modified yeast cell to have a higher survival rate under an acidic condition than a cell of the same type that has not been manipulated. Also, the term "acid resistant" refers to the an ability of a genetically modified yeast cell t to exhibit better metabolic processes (e.g., better "metabolizability") under an acidic condition than a cell of the same type that has not been manipulated. The acidic condition may include an organic acid, an inorganic acid, or a combination thereof. The organic acid may be a C1-C20 organic acid (i.e., an organic acid comprising from about 1 carbon to about 20 carbons). The organic acid may be acetic acid, lactic acid, propionic acid, 3-hydroxy propionic acid, butyric acid, 4-hydroxybutyric acid, succinic acid, fumaric acid, malic acid, oxalic acid, adipic acid, or a combination thereof.

The genetically modified yeast cell may grow better than an unmodified cell of the same type in a pH range of about 2.0 to about 5.0, for example, about 2.0 to about 4.0, about 2.0 to about 3.8, about 2.5 to about 3.8, about 3.0 to about 3.8, about 2.0 to about 3.0, about 2.0 to about 2.7, about 2.0 to about 2.5, or about 2.5 to about 3.0. The "metabolizability" a yeast cell exhibits may be measured through an absorption rate of nutrients for each cell, for example, through an absorption rate of glucose for each cell. Also, the extent of "metabolizability" may be measured through a product release rate, for example, a carbon dioxide release rate of the cell.

In one embodiment, the genetically modified acid-resistant yeast cell may be a lactic acid resistant *Saccharomyces cerevisiae* cell that has a better growth rate in a lactic acid-containing medium than in a lactic acid free medium. For example, the lactic acid resistant *Saccharomyces cerevisiae* cell may have a growth rate that is about 1.6 times to about 12.5 times as great as a growth rate of a an unmodified parent strain, e.g., from about 2.0 to about 10, about 3 to about 12, about 5 to about 11, or about 4 to about 9 times greater than an unmodified parent strain.

Also, the lactic acid resistant *Saccharomyces cerevisiae* cell may have greater lactic acid productivity or yield than a parent cell. For example, the lactic acid resistant *Saccharomyces cerevisiae* cell may have yield that is about 1.4 times to about 13.4 times as great as yield of the parent cell, e.g., from about 2.0 to about 10, about 3 to about 12, about 5 to about 13, or about 4 to about 9 times greater than an unmodified parent strain. The parent strain may include a parent cell or a wild-type cell from which a genetically modified yeast cell has been derived.

The *Saccharomyces cerevisiae* with enhanced acid resistance may be prepared through a mutagen treatment of a *Saccharomyces cerevisiae* cell, particularly a *Saccharomyces cerevisiae* cell that has been previously modified to inactivate or reduce the activity of a polypeptide that converts pyruvate into acetaldehyde, a polypeptide that converts lactate into pyruvate, a polypeptide that converts dihydroxyacetone phosphate (DHAP) into glycerol-3-phosphate, or a combination thereof compared to an unmodified cell of the same type (e.g., native *Saccharomyces cerevisiae*); and to increase the activity of a polypeptide that converts pyruvate into lactate compared to an unmodified cell of the same type (e.g., native *Saccharomyces cerevisiae*). As used herein, the term mutagen treatment refers to exposing a genetically modified yeast cell to chemical agents for a period of time sufficient to cause one or more mutations of the genetic material of the yeast cell. In one embodiment, the mutagen may be a chemical mutagen that introduces GC to AT substitution mutations.

As used herein, the expression "increase in activity" or "increased activity" of an enzyme or a polypeptide may refer to a sufficient increase in the amount thereof or the activity thereof, and may also refer to an activity level of a genetically modified yeast cell or an isolated enzyme produced by a genetically modified yeast cell (i.e., a modified enzyme) that is higher than that of a comparable cell of the same type or an original enzyme of the same type. In other words, the biochemical activity of the polypeptide may be increased by about 5% or more, about 10% or more, about 15% or more, about 20% or more, about 30% or more, about 50% or more, about 60% or more, about 70% or more, or about 100% than the same biochemical activity of an unmanipulated enzyme. The enzyme having increased activity may be identified by using a method known in the art.

The expression "inactivated" or "reduced" activity of the enzyme or the polypeptide or an enzyme having "inactivated" or "reduced" activity refers to an activity level at which a genetically modified yeast cell or an isolated enzyme produced by the genetically modified yeast cell (i.e., modified enzyme) shows no activity or the activity level that is lower than that of a comparable cell of the same type or the original enzyme of the same type. In other words, the conversion activity of the enzyme, which is a conversion activity of an enzyme that converts a substrate into a product, may be decreased by about 20% or more, about 30% or more, about 40% or more, about 50% or more, about 55% or more, about 60% or more, about 70% or more, about 75% or more, about 80% or more, about 85% or more, about 90% or more, about 95% or more, or about 100% than the same biochemical conversion activity of an unmanipulated enzyme. A cell including an enzyme having the decreased activity may be identified by using a method known in the art. The inactivation or decreased activity includes a scenarios in which the enzyme produced by the genetically modified yeast cell is inactive or has reduced activity even when the enzyme is expressed and scenarios in which the gene encoding the enzyme is not expressed or has reduced expression than compared to an unmanipulated gene or the unmanipulated cells.

The inactivation or reduced activity of the enzyme may be due to substitution, addition, or deletion of some portions or all of a gene encoding the enzyme. For example, the inactivation or reduced activity of the enzyme may be caused by a homologous recombination, in which a vector including a sequence of some portions of the gene is transformed into a cell, which is then cultured so that the sequence may be homologously recombined with an endogenous gene of the cell, and then selecting homologously recombined cells by using a selection marker.

The terms "disruption," "disrupted," and the like used herein refers to reduced expression of a given gene due to a genetic modification. Disruption can be caused by a genetic modification that inhibits expression of a referenced gene (hereinafter, referred to as "inactivation" of a gene.) Disruption includes a genetic modification that causes expression of a gene at decreased levels without completely inhibiting expression (hereinafter, referred to as "attenuation" of a gene.). Expression, in this sense, refers to transcription of a gene product as well as translation of an active gene product. Thus, inactivation of a gene includes a case in which a gene is not transcribed or translated, such that the protein product of the gene is not expressed, and a case in which although a gene is transcribed and translated, the gene product is not functional. Similarly, attenuation includes a case in which transcription or translation of a gene is reduced, as well as a case in which transcription or translation is not reduced, but the gene product has a lower activity level. Herein, the term "a functional product of a gene" means that the gene product (e.g., protein or enzyme) of a parent cell or wild-type cell has a biochemical or physiologic function (for example, enzyme activity). The disruption of the gene includes a functional disruption of the gene.

The term "parent cell" used herein refers to a cell prior to a particular genetic modification (e.g., an "original" cell).

For example, in the case of an engineered yeast cell, a yeast cell before being genetically engineered. The "parent cell" is a cell that does not have a particular genetic modification but, in other aspects, the parent cell may be identical to a genetically engineered cell of the same type. Accordingly, the parent cell may be a cell that is used as a starting material for the production of a genetically engineered cell, such as a yeast cell having increased or decreased activity of a particular protein or enzyme.

The term "gene" as used herein refers to a nucleic acid fragment expressing a specific protein and may or may not include a regulatory sequence such as 5'-non-coding sequence and/or 3'-non-coding sequence.

The term "sequence identity" of a nucleic acid or a polypeptide according to an embodiment of the present invention refers to the extent of identity between bases or amino acid residues of sequences after aligning the sequences such that they maximally match in certain comparative regions. The sequence identity is a value calculated by optimally aligning two sequences at certain comparative regions, wherein portions of the sequences at the certain comparative regions may be added or deleted compared to reference sequences. A percentage of sequence identity may be calculated by, for example, comparing two optimally aligned sequences in the entire comparative region, determining the number of locations in which the same amino acids or nucleic acids appear to obtain the number of matched locations, dividing the number of the matched locations by the total number of locations in the comparative region (that is, the size of the range), and multiplying 100 thereto to calculate the percentage of the sequence identity. The percentage of the sequence identity may be calculated by using a known sequence comparison program, and examples of such a program include BLASTN (NCBI), CLC Main Workbench (CLC bio), and MegAlign™ (DNASTAR Inc).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

The mutagen may include a chemical mutagen. The chemical mutagen may be ethyl methane sulfonate (EMS), ethyl ethane sulfonate (EES), methyl methane sulfonate (MMS), N'-nitro-N-ninitrosoguanidine (NTG), ethylene oxide (EO), proflavine, acridine orange, 4-nitroqyinoline 1-oxide (4-NQO), nitrous acid ($HNO_2$), hydroxylamine ($NH_2OH$), dimethyl sulfate (DMS), diethyl sulfate (DES), N-methylcarbazole (NMC), N-nitroso-N-methylurea, N-ethyl-N'-nitro-N-nitrosoguanidine (ENNG), N-methyl-N'-nitro-N-nitrosoguanidine (MNNG), N-ethyl-N-nitrosurea (ENU), N-methyl-N-nitrosourea (MNU), aminocytidine, diazouracil, azacytidine, aminopurine, mercaptopurine, glyoxal, formaldehyde, cumene hydroperoxide (CHP), t-butyl hydroperoxide (BHP), AF-2(2-(2-furyl)-3-(5-nitro-2-furyl) acrylamide), captan, phosmet, or $NaN_3$. In one embodiment, the mutagen may be a chemical that causes substitution of G-C base pairs with A-T base pairs. For example, exposure of a yeast cell to EMS may cause a change a structure of guanine (G) into O-6-ethylguanine. During DNA replication, the O-6-ethylguanine will pair with thymine (T) instead of cytosine (C). Repeated rounds of replication may then result in one or more G-C base pairs to be replaced with A-T base pairs.

The concentration (e.g., volume of EMS per volume of cell culture media) of the chemical mutagen (e.g., EMS) that the yeast cell is exposed to may be about 1% to about 5% (v/v), about 1.5% to about 4.5% (v/v), about 2% to about 4% (v/v), about 2.5% to about 3.5% (v/v), or about 3% (v/v). The time the yeast cell is exposed to the chemical mutagen (e.g., EMS) may be about 15 minutes to about 90 minutes, about 30 minutes to about 90 minutes, about 45 minutes to about 90 minutes, about 60 minutes to about 90 minutes, or about 75 minutes to about 90 minutes.

Mutagen treatment of genetically modified yeast cell can result in the formation of a variant strain of the genetically modified yeast cell with acid-resistance and increased growth and/or metabolic activity compared to a non-variant strain of the genetically modified yeast cell. In one embodiment, the mutagen-treated yeast cell may be cultured, and the cultured yeast cells may be selected to obtain lactic acid resistant *Saccharomyces cerevisiae*, which may have an accession number of KCTC 12532BP. The selection of an acid resistant variant strain of the genetically modified yeast cell from the cell culture medium may be performed by selecting yeast cells which exhibit increased growth, metabolic activity, and/or acid resistance compared to non-variant strains of the same type in the cell culture medium after incubation for a period of time. For example, selection can comprise incubation of the mutagen treated cells in a cell culture medium having a pH from about 2.0 to about 5.0 for a period of time and selection of surviving colonies, which exhibit increased growth and/or metabolic activity compared to a nonmutagen treated yeast cells of the same type.

The *Saccharomyces cerevisiae* to be treated with a mutagen may be a strain engineered to inactivate or reduce the activity of a polypeptide that converts pyruvate into acetaldehyde compared to an unmodified cell of the same type. The polypeptide that converts pyruvate into acetaldehyde may be an enzyme that is classified as EC 4.1.1.1. For example, the polypeptide may be a pyruvate decarboxylase. The polypeptide that converts pyruvate into acetaldehyde may have an amino sequence SEQ ID NO: 1 and an amino acid sequence having a sequence identity of 50% or greater, 70% or greater, 80% or greater, 90% or greater, 95% or greater, 96% or greater, 97% or greater, 98% or greater, 99% or greater, or 100%. The gene that codes the polypeptide that converts pyruvate into acetaldehyde may include a nucleotide sequence of SEQ ID NO: 4. The gene may be pdc1 that codes for pyruvate decarboxylase (Pdc).

The *Saccharomyces cerevisiae* to be treated with a mutagen may be a strain engineered to inactivate or reduce the activity of a polypeptide that additionally converts lactate into pyruvate compared to an unmodified cell of the same type. The polypeptide that converts lactate into pyruvate may be a cytochrome c-dependent enzyme. The polypeptide that converts lactate into pyruvate may be a lactate cytochrome-c oxidoreductase (Cyb2). The lactate cytochrome c-oxydoreductase may be an enzyme that is classified as EC 1.1.2.4, which acts on D-lactate or EC 1.1.2.3, which acts on L-lactate. The polypeptide that converts lactate into pyruvate may include an amino acid sequence having a sequence identity to an amino acid sequence of SEQ ID NO: 2 of about 50% or greater, 70% or greater, 80% or greater, 90% or greater, 95% or greater, 96% or greater, 97% or greater, 98% or greater, 99% or greater, or 100%. The gene that codes for a polypeptide that converts lactate into pyruvate may have a nucleotide sequence of SEQ ID NO: 5.

The *Saccharomyces cerevisiae* to be treated with a mutagen may be a strain engineered to inactivate or reduce the activity of a polypeptide that additionally converts DHAP into glycerol-3-phosphate compared to an unmodified cell of the same type. The polypeptide that additionally converts DHAP into glycerol-3-phosphate may be a cytosol glycerol-3-phosphate dehydrogenase may be an enzyme that catalyzes reduction of DHAP into glycerol-3-phosphate through an oxidation of NADH into $NAD^+$. The Gpd1 may belong to EC 1.1.1.8. The Gpd1 may have an amino acid sequence having a sequence identity to an amino acid sequence of SEQ ID NO: 3 of about 50% or greater, 70% or greater, 80% or greater, 90% or greater, 95% or greater, 96% or greater, 97% or greater, 98% or greater, 99% or greater, or 100%. The gene that encodes the Gpd1 may have a nucleotide sequence of SEQ ID NO: 6.

The *Saccharomyces cerevisiae* to be treated with a mutagen may be engineered to have an increased rate of conversion of pyruvate into lactate compared to an unmodified cell of the same type. The conversion of pyruvate into lactate may be sufficiently increased to produce lactate. The conversion of pyruvate into lactate may be increased due to increased insertion and expression of the polypeptide that converts pyruvate into lactate into the yeast cell. The increased expression may be due to increased copy number of the gene or changes to a regulatory sequence of the gene. The increased copy number of the gene may be due to an amplification of an endogenous gene or introduction of an exogenous gene. The mutation of the regulatory region of the gene may be caused by mutation of a regulatory region of the endogenous gene. The exogenous gene may be a homogenous or a heterogeneous gene.

The polypeptide that converts pyruvate into lactate may be a lactate dehydrogenase. The lactate dehydrogenase may catalyze conversion of pyruvate into lactate. The lactate dehydrogenase may be an NAD(P)-dependent enzyme and may also act on L-lactate or D-lactate. The NAD(P)-dependent enzyme may be an enzyme classified as EC 1.1.1.27, which acts on L-lactate or as EC 1.1.1.28, which acts on D-lactate.

A polynucleotide that encodes the lactate dehydrogenase may be derived from bacteria, yeast, fungi, a mammal, or a reptile. The polynucleotide may a polynucleotide encoding at least one lactate dehydrogenase selected from *Pelodiscus sinensis japonicus, Ornithorhynchus anatinus, Tursiops truncatus, Rattus norvegicus,* or *Xenopus laevis.* The lactate dehydrogenase derived from *Pelodiscus sinensis japonicus,* the lactate dehydrogenase derived from *Ornithorhynchus anatinus,* the lactate dehydrogenase derived from *Tursiops truncatus,* and the lactate dehydrogenase derived from *Rattus norvegicus* may have an amino acid sequence having a sequence identity of about 50% or greater, 70% or greater, 80% or greater, 90% or greater, 95% or greater, 96% or greater, 97% or greater, 98% or greater, 99% or greater, or 100% to SEQ ID NO: 7, 8, 9, and 10, respectively. The gene encoding the lactate dehydrogenase may have a nucleotide sequence of SEQ ID NO: 11.

The polynucleotide coding for the Ldh may be a vector including an Ldh derived from bacteria, yeast, fungi, a mammal, or a reptile. The vector may include an origin of replication, a promoter, a polynucleotide coding for a lactate dehydrogenase, and a terminator. The origin of replication may include an autonomous replication sequence (ARS). The ARS may be stabilized by a centrometric sequence (CEN). The promoter may be selected from the group consisting of a CYC promoter, a TEF promoter, a GPD promoter, and an ADH promoter. The CYC promoter, the TEF promoter, the GPD promoter, and the ADH promoter may include nucleotide sequences having SEQ ID NO: 13, 14, 15, and 16. The terminator may be selected from the group consisting of phosphoglycerate kinase 1 (PGK1), cytochrome c transcription (CYC1), and GAL1. The CYC1 terminator may have a nucleotide sequence of SEQ ID NO: 17. The vector may further include a selection marker.

The polynucleotide coding for Ldh may be included in a genome of a yeast cell. When the polynucleotide coding for Ldh produces an active protein in a cell, the polynucleotide is considered as "functional" in the cell. The yeast cell including the polynucleotide coding for an L-lactate dehydrogenase or a D-lactate dehydrogenase may produce an L-lactate enantiomer or a D-lactate enantiomer, or a salt thereof.

The *Saccharomyces cerevisiae* to be treated with a mutagen may include a polynucleotide coding for a single Ldh or a polynucleotide coding for a plurality of Ldhs having a copy number of 1 to 10. The polynucleotide coding for the plurality of Ldhs may be a polynucleotide coding for an Ldh having a copy number of 1 to 8, 1 to 7, 1 to 6, 1 to 5, 1 to 4, or 1 to 3. When the yeast cell includes the polynucleotide coding for the plurality of Ldhs, each polynucleotide may include a copy of the same polynucleotide or a copy of a polynucleotide coding for two or more different Ldhs. A plurality of copies of a polynucleotide coding for an exogenous Ldh may be included in the same locus or in many loci in a genome of a host cell.

Also, the *Saccharomyces cerevisiae* cell to be treated with a mutagen may be a strain engineered to inactivate or reduce the activity of a polypeptide that converts pyruvate into acetaldehyde, a polypeptide that converts lactate into pyruvate, a polypeptide that converts DHAP into glycerol-3-phosphate, or a combination thereof compared to an unmodified cell of the same type and has increased activity of a polypeptide that converts pyruvate into lactate compared to an unmodified cell of the same type.

As a specific example of a *Saccharomyces cerevisiae* to be treated with a mutagen, the *Saccharomyces cerevisiae* may be a strain deposited in Korean Collector for Type Culture (KCTC) on May 30, 2013 under accession number KCTC 12415BP.

Also provided is a method of preparing a variant strain of *Saccharomyces cerevisiae,* the method comprising treating *Saccharomyces cerevisiae* yeast cells with a mutagen; culturing mutagen-treated yeast cells; and selecting cultured the yeast cells that grow in the cell culture medium. By treating genetically modified *Saccharomyces cerevisiae* yeast cells with a mutagen, the mutagen causes a mutation in at least one genetically modified *Saccharomyces cerevisiae* yeast cell to form a variant strain of genetically modified *Saccharomyces cerevisiae.* Culturing mutagen-treated genetically modified *Saccharomyces cerevisiae* yeast cells in a cell culture medium having a pH from about 2.0 to about 5.0, whereby the variant strain of genetically modified *Saccharomyces cerevisiae* with greater acid resistance grows at a higher rate compared to other strains. Selecting the variant strain of genetically modified *Saccharomyces cerevisiae* from the cell culture medium based upon the higher growth rate of the acid-resistant variant strain thereby allows selection of a desired variant strain with acid resistance.

All aspects of the *Saccharomyces cerevisiae* prepared according to the method are as described herein with respect to other embodiments. Thus, for instance, the variant strain of *Saccharomyces cerevisiae* may have acid-resistance to lactic acid having a pH of about 2.0 to about 5.0.

The mutagen may include a chemical mutagen. The chemical mutagen may be EMS, EES, MMS, N'-nitro-N-ninitrosoguanidine (NTG), EO, proflavine, acridine orange, 4-NQO, $HNO_2$, $NH_2OH$, DMS, DES, NMC, N-nitroso-N-methylurea, ENNG, MNNG, ENU, MNU, aminocytidine, diazouracil, azacytidine, aminopurine, mercaptopurine, glyoxal, formaldehyde, CHP, BHP, AF-2(2-(2-furyl)-3-(5-nitro-2-furyl)acrylamide), captan, phosmet, or $NaN_3$. For example, treating of the NTG to a microorganism may produce mutant from the microorganism which is able to grow in an acidic condition (see Sheng Wu Gong Cheng Xue Bao. (Liu et al.) "Breeding of monofluoroacetate-resistant strains of *Actinobacillus succinogenes* and the mechanism based on metabolic flux analysis," 2008 March; 24(3):460-7.). In one embodiment, the mutagen may be a chemical that causes substitution of G-C base pairs with A-T base pairs, such as EMS.

In the method described above, a concentration of the EMS may be about 1% (v/v) to about 5% (v/v), about 1.5% (v/v) to about 4.5% (v/v), about 2% (v/v) to about 4% (v/v), about 2.5% to about 3.5% (v/v), or about 3% (v/v). Also, treatment duration of the EMS may be about 15 minutes to about 90 minutes, about 30 minutes to about 90 minutes, about 45 minutes to about 90 minutes, about 60 minutes to about 90 minutes, or about 75 minutes to about 90 minutes.

In the method described above, the yeast cell to be treated with a mutagen may be modified (genetically engineered) to inactivate or reduce the activity of a polypeptide that converts pyruvate into acetaldehyde, a polypeptide that converts lactate into pyruvate, a polypeptide that converts DHAP into glycerol-3-phosphate, or a combination thereof compared to an unmodified yeast cell of the same type, and to increase the activity of a polypeptide that converts pyruvate into lactate. The *Saccharomyces cerevisiae* cell may be as described above compared to an unmodified yeast cell of the same type. Such modifications are described in greater detail with respect to other embodiments.

According to another embodiment, provided is a method of preparing lactate, the method including culturing an acid-resistant yeast cell described herein to obtain cultured products; and retrieving lactate from the cultured products.

The culturing may be performed in a culture medium including a carbon source, for example, glucose. The culture medium used for culturing the yeast cells may be any general medium that is suitable for growth of host cells, such as a minimum or composite medium including suitable supplements. The suitable medium may be a commercially available medium or may be prepared according to a method known in the art.

The culture medium may be a medium that satisfies requirements of a specific yeast cell. The medium may be a medium selected from the group consisting of a carbon source, a nitrogen source, a salt, a trace element, and a combination thereof. The pH of a fermented solution may be maintained at about 2 to about 7.

The yeast cell may be cultured by a continuous method, a semi-continuous method, a batch-wise method, or a combination method thereof.

Culturing conditions of genetically manipulated yeast cells may be suitably adjusted to obtain lactate. The cells may be cultured under an aerobic or anaerobic condition. For example, the cells may be cultured under an aerobic condition to proliferate the same and then cultured under an anaerobic condition to produce lactate. The anaerobic condition may include a microaerobic condition in which a concentration of dissolved oxygen (DO) is about 0% to about 10%, for example, about 0% to about 8%, about 0% to about 6%, about 0% to about 4%, or about 0% to about 2%.

The term "culturing condition" refers to a condition for culturing yeast cells. The culturing condition may be, for example, a carbon source, a nitrogen source, or an oxygen condition used by the yeast cells. A carbon source that is usable for the yeast cells include monosaccharides, disaccharides, and polysaccharides. In more detail, glucose, fructose, mannose, or galactose may be used. The nitrogen source usable for the yeast cells may be organic nitrogen compounds or inorganic nitrogen compounds. The nitrogen source may be amino acids, amides, amines, nitrates, or ammonium salts. Oxygen conditions for culturing the yeast cells include an aerobic condition at a normal oxygen partial pressure, a low oxygen condition including about 0.1% to about 10% of oxygen or an anaerobic condition free of oxygen. A metabolic pathway may be modified according to a usable carbon source or nitrogen source of the yeast cells.

Separation of lactate from cultured products may be any general method known in the art. The method may be centrifugation, filtration, ion exchange chromatography, or crystallization. For example, the cultured products may be centrifuged at a low speed to remove biomass and separate a supernatant solution obtained therefrom through the ion exchange chromatography.

One or more embodiments of the present invention will now be described in further detail with reference to the following Examples. However, these examples are for the illustrative purposes only and are not intended to limit the scope of the invention.

Example 1

Preparation of a Strain and an Expression Vector for Highly Efficient Production of Lactate

*Saccharomyces cerevisiae* CEN.PK2-1D (MATα ura3-52; trp1-289; leu2-3,112; his3 Δ 1; MAL2-8$^C$; SUC2, EUROSCARF accession number: 30000B) was used as a lactate producing strain. To block a production pathway for ethanol and glycerol, which are main by-products, a gene coding for a pyruvate decarboxylase (pdc1), which is a main enzyme for alcohol fermentation, a gene coding for an NAD-dependent glycerol-3-phosphate dehydrogenase (gpd1), which is a main enzyme for glycerol biosynthesis, and a gene coding for an L-lactate cytochrome-c oxidoreductase2 (cyb2), which is a lactate lyase, were inactivated through a homologous recombination.

(1.1) Preparation of L-Ldh Over-Expression Vector and an Inactivating Vector for pdc1, gpd1, and cyb2 Genes (1.1.1) Preparation of an L-Ldh Over-Expression Vector For over-expression of L-Ldh, genomic DNA of *Saccharomyces cerevisiae* CEN.PK2-1D was used as a template and PCR fragments of a CCW12 promoter obtained through PCR by using primers for SEQ ID NO: 18 and 19 were excised by using SacI and XbaI, and excised fragments were inserted into a p416-GPD, which was a GPD promoter excised with SacI and XbaI, to prepare p416-CCW12p.

Thereafter, genomic DNA of L-ldh (SEQ ID NO: 7) derived from *Pelodiscus sinensis japonicas* was used as a template and primers for SEQ ID NO: 20 and 21 were used to perform PCR, and then PCR fragments obtained therefrom and p416-CCW12p were excised by using BamHI and SalI and then ligated to prepare p416-CCW12p-LDH, which was an L-ldh expression vector.

Also, the L-ldh expression vector includes a self-replicating sequence of yeast/yeast centromeric sequence of SEQ ID NO: 12, a CYC promoter of SEQ ID NO: 13, a GPD promoter of SEQ ID NO: 15, and a CYC1 terminator of SEQ ID NO: 17, and a polynucleotide coding for an L-ldh of SEQ ID NO: 7 derived from *Pelodiscus sinensis japonicas*.

FIG. 1 is a view showing a p416-CCW12p-LDH vector. As shown in FIG. 1, the vector includes a gene for coding Ldh derived from *Pelodiscus sinensis japonicas* integrated therein.

(1.1.2) Preparation of a Gene Exchange Vector

Figure 2:
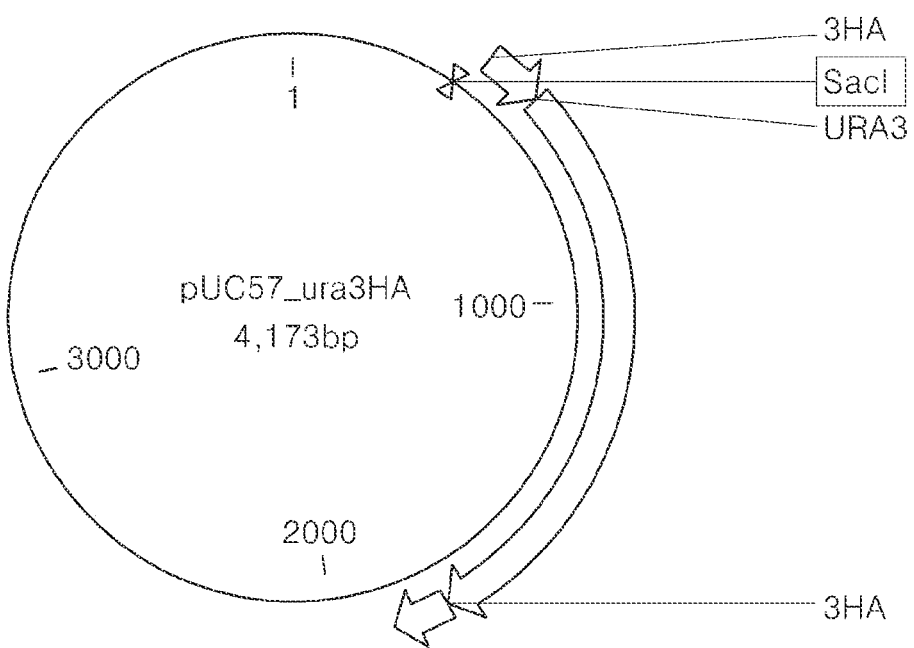
FIG. 2 is a vector map of a pUC57-ura3HA vector.
Figure 3:
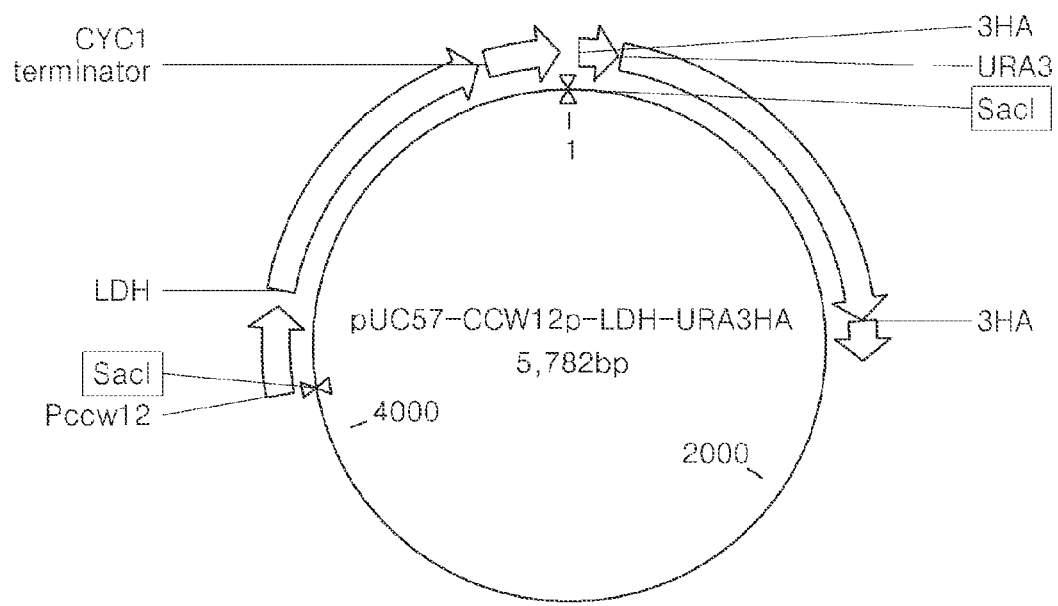
FIG. 3 is a vector map of a pUC57-CCW12p-LDH-ura3HA vector.

While deleting genes coding for Pdc1, Cyb2, and Gpd1 by homologous recombination, a gene exchange vector was prepared as below to insert an L-ldh gene thereto. FIG. 2 is a view showing a pUC57-ura3HA (Genetics 116: 541-545, August, 1987). FIG. 3 is a view showing a pUC57-CCW12p-LDH-ura3HA vector.

p416-CCW12p-LDH was used as a template, PCR was performed by using primers having SEQ ID NO: 22 and 23, and PCR fragments and a pUC57-ura3HA vector obtained therefrom were excised by using SacI, which were then ligated to prepare pUC57-CCW12p-LDH-ura3HA.

The pUC57-CCW12p-LDH-ura3HA obtained above was used as a template, and primers of SEQ ID NO: 24 and 25 were used to perform PCR to prepare a pdc1 gene deletion cassette.

The pUC57-CCW12p-LDH-ura3HA was used as a template, and primers of SEQ ID NO: 26 and 27 were used to perform PCR to prepare a cyb2 gene deletion cassette.

The pUC57-CCW12p-LDH-ura3HA was used as a template, and primers of SEQ ID NO: 28 and 29 were used to perform PCR to prepare a gpd1 gene deletion cassette.

(1.2) Inactivation of Pdc1, Gpd1, and Cyb2 Genes

A variant strain in which a gene coding for Pdc1 was deleted from *Saccharomyces cerevisiae* CEN.PK2-1D was prepared as follows: *Saccharomyces cerevisiae* CEN.PK2-1D was smeared on YPD (10 g of yeast extract, 20 g of peptone, and 20 g of glucose) solid medium to culture the same for about 24 hours at a temperature of about 30° C., and the colony was inoculated in about 10 ml of a YPD liquid medium to culture for about 18 hours at a temperature of about 30° C. A sufficiently grown culture medium was inoculated at 1% (v/v) in 50 ml of a YPD liquid medium in a 250 ml flask to culture the same at a speed of about 230 rpm and at a temperature of about 30° C. in an incubator. After about 4 hours to about 5 hours, when $OD_{600}$ reached about 0.5, cultured cells were centrifuged at a speed of about 4,500 rpm for about 10 minutes to retrieve the cells and then resuspended in a lithium acetate solution having a concentration of about 100 mM. Thereafter, the cells were centrifuged at a speed of about 4,500 rpm for about 10 minutes to retrieve the cells, resuspended in a lithium acetate solution having a concentration of about 1M including about 15% glycerol, and then the cells were divided into about 100 μl.

To remove pdc1 gene, the pdc1 gene deletion cassette manufactured in Example 1.1.2 was mixed with 50% polyethylene glycol and single stranded carrier DNA, which were reacted in a water bath at a temperature of about 42° C. for about 1 hour and then the culture medium obtained therefrom was smeared and cultured in a uracil-free minimum solid medium (YSD, 6.7 g/L of yeast nitrogen base without amino acids and 1.4 g/L of Amino acid dropout mix (−ura)) at a temperature of about 30° C. for 24 hours or more. 10 colonies selected from colonies (variant strains) formed on the plate were moved again to a uracil-free minimum solid medium while culturing the colonies in a liquid medium having the same composition to separate genomic DNA from the strain by using a commercial kit (Gentra Puregene Cell kit, Qiagen, USA). The separated variant genomic DNA was used as a template to perform PCR by using primers of SEQ ID NO: 30 and 31 and confirm deletion of pdc1 gene, and PCR products obtained therefrom were subjected to electrophoresis to confirm pdc1 gene deletion. As a result, *Saccharomyces cerevisiae* CEN.PK2-1D (Δ pdc1::ldh+ura3) was obtained.

Also, for deletion of an additional gene by using the gene deletion vector, an URA3 gene, which was a selection marker for a pdc1 gene deletion cassette that was integrated to prepare a CEN.PK2-1D (Δ pdc1::ldh+ura3) strain, was removed as follows: *Saccharomyces cerevisiae* CEN.PK2-1D (Δ pdc1+ldh) was inoculated in about 10 ml of a YPD liquid medium to culture the same for about 18 hours at a temperature of about 30° C., then smeared on 5-FOA (YSD, 6.7 g/L of yeast nitrogen base without amino acids, 1.4 g/L of Amino acid dropout mix, and 1 μg/L of 5-Fluoroorotic Acid) solid medium to culture the same at a temperature of about 30° C. for 24 hours or more. 10 colonies formed on the plate (URA3 pop-out strains) were selected and then moved to a 5-FOA solid medium while culturing the same in a YPD liquid medium to separate a genomic DNA from the strain by using a commercial kit (Gentra Puregene Cell kit, Qiagen, USA). PCR was performed by using genomic DNA of the URA3 pop-out strain as a template and primers of SEQ ID NO: 30 and 31 to confirm deletion of URA3, and PCR products obtained therefrom were subjected to electrophoresis to confirm the deletion of URA3. As a result, *Saccharomyces cerevisiae* CEN.PK2-1D (Δ pdc1::ldh) was obtained.

A variant strain in which a gene for coding Cyb2 in *Saccharomyces cerevisiae* CEN.PK2-1D (Δ pdc1::ldh) was deleted was prepared as follows: The *Saccharomyces cerevisiae* CEN.PK2-1D (Δ pdc1::ldh) was smeared on a YPD (10 g of yeast extract, 20 g of peptone, and 20 g of glucose) solid medium and cultured for about 24 hours at a temperature of about 30° C., and a colony obtained therefrom was inoculated in about 10 ml of a YPD liquid medium for about 18 hours at a temperature of about 30° C. A sufficiently grown culture medium was inoculated at 1% (v/v) in 50 ml of a YPD liquid medium in a 250 ml flask to culture the same at a speed of about 230 rpm and at a temperature of about 30° C. in an incubator. After about 4 hours to about 5 hours, when $OD_{600}$ reached about 0.5, cultured cells were centrifuged at a speed of about 4,500 rpm for about 10 minutes to retrieve the cells, which were resuspended in a lithium acetate solution having a concentration of about 100 mM. Thereafter, the cells were centrifuged at a speed of about 4,500 rpm for about 10 minutes to retrieve the cells, and resuspended in a lithium acetate solution having a concentration of about 1 M including about 15% glycerol, and then the cells were divided into about 100 ul.

To remove cyb2 gene, the same method as used in the deletion of pdc1 gene was used. The cyb2 gene deletion cassette manufactured in Example 1.1.2 was mixed with 50% polyethylene glycol and single stranded carrier DNA, which were reacted in a water bath at a temperature of about 42° C. for about 1 hour, and then the culture medium obtained therefrom was smeared and cultured in a uracil-free minimum solid medium (YSD, 6.7 g/L of yeast nitrogen base without amino acids, 1.4 g/L of Amino acid dropout mix (−ura)) at a temperature of about 30° C. for 24 hours or more. 10 colonies selected from colonies (variant strains) formed on the plate were moved again to a uracil-free minimum solid medium while culturing the colonies in a liquid medium having the same composition to separate genomic DNA by using a commercial kit (Gentra Puregene Cell kit, Qiagen, USA). The separated variant genomic DNA was used as a template, and PCR was performed by using primers of SEQ ID NO: 32 and 33 to confirm deletion of cyb2 gene, and PCR products obtained therefrom were subjected to electrophoresis to confirm cyb2 gene deletion. As a result, *Saccharomyces cerevisiae* CEN.PK2-1D (Δ pdc1::ldh Δ cyb2::ldh+ura3) was obtained.

Also, for deletion of an additional gene by using the gene deletion vector, a URA3 gene, which was a selection marker for a cyb2 gene, was removed by using a URA3 pop-out method. *Saccharomyces cerevisiae* CEN.PK2-1D (Δ pdc1::ldh Δ cyb2::ldh+ura3) was inoculated in about 10 ml of a YPD liquid medium to culture the same for about 18 hours at a temperature of about 30° C., and then smeared on a 5-FOA (YSD, 6.7 g/L of yeast nitrogen base without amino acids, 1.4 g/L of Amino acid dropout mix, and 1 µg/L of 5-Fluoroorotic Acid) solid medium to culture the same at a temperature of about 30° C. for 24 hours or more. 10 colonies formed on the plate (a URA3 pop-out strain) were selected and then moved to a 5-FOA solid medium while culturing the same in a YPD liquid medium to separate a genomic DNA from the strain by using a commercial kit (Gentra Puregene Cell kit, Qiagen, USA). PCR was performed by using genomic DNA of the URA3 pop-out strain as a template and primers of SEQ ID NO: 32 and 33 to confirm deletion of URA3, and PCR products obtained therefrom were subjected to electrophoresis to confirm the deletion of URA3. As a result, *Saccharomyces cerevisiae* CEN.PK2-1D (Δ pdc1::ldh Δ cyb2::ldh) was obtained.

A variant strain in which a gene coding for Gpd1 in *Saccharomyces cerevisiae* CEN.PK2-1D (Δ pdc1::ldh Δ cyb2::ldh) was deleted was prepared as follows: The *Saccharomyces cerevisiae* CEN.PK2-1D (Δ pdc1::ldh Δ cyb2::ldh) was smeared on a YPD (10 g of yeast extract, 20 g of peptone, and 20 g of glucose) solid medium, cultured for about 24 hours at a temperature of about 30° C., and a colony obtained therefrom was inoculated in about 10 ml of a YPD liquid medium for about 18 hours at a temperature of about 30° C. A sufficiently grown culture medium was inoculated at 1% (v/v) in 50 ml of a YPD liquid medium in a 250 ml flask to culture the same at a speed of about 230 rpm and at a temperature of about 30° C. in an incubator. After about 4 hours to about 5 hours, when $OD_{600}$ reached about 0.5, cultured cells were centrifuged at a speed of about 4,500 rpm for about 10 minutes to retrieve the cells and then resuspended in a lithium acetate solution having a concentration of about 100 mM. Thereafter, the cells were centrifuged at a speed of about 4,500 rpm for about 10 minutes to retrieve the cells, resuspended in a lithium acetate solution having a concentration of about 1M including about 15% glycerol, and divided into about 100 µl.

To remove a gpd1 gene, the same method as used in the deletion of pdc1 gene and cyb2 was used. The gpd1 gene deletion cassette manufactured in Example 1.1.2 was mixed with 50% polyethylene glycol and single stranded carrier DNA, which was reacted in a water bath at a temperature of about 42° C. for about 1 hour, and then the culture medium was smeared and cultured in a uracil-free minimum solid medium (YSD, 6.7 g/L of yeast nitrogen base without amino acids, 1.4 g/L of Amino acid dropout mix (−ura)) at a temperature of about 30° C. for 24 hours or more. 10 colonies selected from colonies (variant strains) formed on the plate were moved again to a uracil-free minimum solid medium while culturing the colonies in a liquid medium having the same composition to separate genomic DNA by using a commercial kit (Gentra Puregene Cell kit, Qiagen, USA). The separated variant genomic DNA was used as a template, and PCR was performed by using primers of SEQ ID NO: 34 and 35 to confirm deletion of gpd1 gene, and PCR products obtained therefrom were subjected to electrophoresis to confirm gpd1 gene deletion. As a result, *Saccharomyces cerevisiae* CEN.PK2-1D (Δ pdc1::ldh Δ cyb2::ldh Δ gpd1::ldh+ura3) was obtained.

Also, for deletion of an additional gene by using the gene deletion vector, a URA3 gene, which was a selection marker for a gpd1 gene deletion, was removed by using a URA3 pop-out method described above. *Saccharomyces cerevisiae* CEN.PK2-1D (Δ pdc1::ldh Δ cyb2::ldh Δ gpd1::ldh+ura3) was inoculated in about 10 ml of a YPD liquid medium to culture the same for about 18 hours at a temperature of about 30° C., then smeared on a 5-FOA (YSD, 6.7 g/L of yeast nitrogen base without amino acids, 1.4 g/L of Amino acid dropout mix, and 1 µg/L of 5-Fluoroorotic Acid) solid medium to culture the same at a temperature of about 30° C. for 24 hours or more. 10 colonies formed on the plate (a URA3 pop-out strain) were selected and then moved to a 5-FOA solid medium while culturing the same in a YPD liquid medium to separate a genomic DNA from the strain by using a commercial kit (Gentra Puregene Cell kit, Qiagen, USA). PCR was performed by using genomic DNA of the URA3 pop-out strain as a template and primers of SEQ ID NO: 34 and 35 to confirm deletion of URA3, and PCR products obtained therefrom were subjected to electrophoresis to confirm the deletion of URA3. As a result, *Saccharomyces cerevisiae* CEN.PK2-1D (Δ pdc1::ldh Δ cyb2::ldh Δ gpd1::ldh) was obtained.

*Saccharomyces cerevisiae* CEN.PK2-1D (Δ pdc1::ldh Δ cyb2::ldh Δ gpd1::ldh) was deposited and accepted in Korean Collector for Type Culture (KCTC), Biological Research Center, Korea Research Institute of Bioscience and Biotechnology (KRIBB), 181 Ipsin-gil, Jeongeup-si, Jeollabuk-do 56212, Korea on May 30, 2013 and received an accession number of KCTC 12415BP.

Example 2

Preparation of a Mutant Strain Due to Chemical Mutation

To prepare a mutant strain of *Saccharomyces cerevisiae* CEN.PK2-1D (Δ pdc1::ldh Δ cyb2::ldh Δ gpd1::ldh) (accession number: KCTC 12415BP) prepared in Example 1, mutation was induced thereto by using EMS and the process was performed as follows.

A cell concentration in 50 ml of a *Saccharomyces cerevisiae* CEN.PK2-1D (Δ pdc1::ldh Δ cyb2::ldh Δ gpd1::ldh) culture medium was concentrated from an amount in which an optical density (OD) thereof reached 10 from 0.5 in about 600 nm until the OD by using a spectrophotometer, such that a colony obtained therefrom included about $1 \times 10^8$ cells. From the concentrated culture medium obtained therefrom, 1 ml of the culture medium was moved to a 15 ml tube. The 15 ml tube was centrifuged and a supernatant obtained therefrom was discarded, and was washed with 5 ml of distilled water. Thereafter, a supernatant solution obtained therefrom was discarded and 1.7 ml of the culture medium was resuspended in 0.1 M sodium phosphate buffer at pH 7. 50 µl of about 3% (v/v) ethyl methane sulfonate (Sigma, M08880, Liquid) was treated for about 15 minutes to about 90 minutes at an interval of 15 minutes in a 50 µl sterilized glass test tube. The culture medium obtained therefrom was inoculated in a roller shaker.

Example 3

Selection of Mutant Strain Cells

Thereafter, the following processes were performed to retrieve cells in which mutation was induced by ethyl methane sulfonate. Selection of mutants was performed under lactic acid stress condition, i.e., on a plate at pH about 3.1. Under the plate of pH about 3.1, the parent cell of the mutant strain, i.e., *Saccharomyces cerevisiae* CEN.PK2-1D (Δ pdc1::ldh Δ cyb2::ldh Δ gpd1::ldh) (accession number: KCTC 12415BP) did not produce colonies.

At an interval of about 15 minutes, 8 ml of 5% sterilized sodium thiosulfate ($NaS_2O_3$) was added to stop a mutation inducing reaction. In more detail, tubes were prepared to add the sterilized sodium thiosulfate to each tube. Thereafter, the tubes were washed with 9 ml of distilled water. Cells obtained therefrom were diluted to $10^{-4}$, and then 100-200 colony/0.1 mL was smeared on the plate to measure a cell survival rate. The point at which the cell survival rate was about 10% from about 60-70% was viewed as a mutation induction point due to ethyl methane sulfonate, and the cells at this about 10% point were retrieved and selected.

1000 μl of a supernatant solution including selected cells was smeared on 10 ml of a YPD (10 g of yeast extract, 20 g of peptone, and 20 g of glucose) solid medium, cultured for about 18 hours at a temperature of about 30° C., and the colony obtained therefrom was inoculated in 10 ml of a YPD liquid medium to culture the same for about 18 hours at a temperature of about 30° C. A sufficiently grown culture medium was inoculated at 1% (v/v) in 50 ml of a YPD liquid medium in a 250 ml flask to culture the same at a speed of about 230 rpm and at a temperature of about 30° C. in an incubator. After about 4 hours to about 5 hours, when $OD_{600}$ reached about 0.5, cultured cells were centrifuged at a speed of about 4,500 rpm for about 10 minutes to retrieve *Saccharomyces cerevisiae* cells, which were diluted with sterilized water and then smeared on a solid medium. Cells obtained therefrom were diluted to $10^{-3}$ and then smeared about 500~1000 colony/0.1 mL on the plate.

Example 4

Growth Analysis of Selected Lactic Acid Resistant Yeast Cells

A strain selected in Example 3 was cultured under an aerobic condition. Culture conditions were as follows: In a 250 ml flask, 50 ml of a lactic acid medium (pH 3.2) including 2% glucose, 4% lactic acid, 1% yeast extract, and 2% Bacto-peptone were cultured under an aerobic condition at a speed of 230 rpm and at a temperature of about 30° C. An OD value of initial cells was about 0.1. *Saccharomyces cerevisiae* CEN.PK2-1D (Δ pdc1::ldh Δ cyb2::ldh Δ gpd1::ldh) cells were used as a control group.

OD values of the two samples were measured by using a 600 nm spectrophotometer (DU730, Beckman Coulter) for first 64 hours and consumption amounts of lactic acid and sugar were measured by high performance liquid chromatography (HPLC) (Alliance 2695, Waters). Results obtained therefrom are shown as an average value of the two samples.

Figure 4:
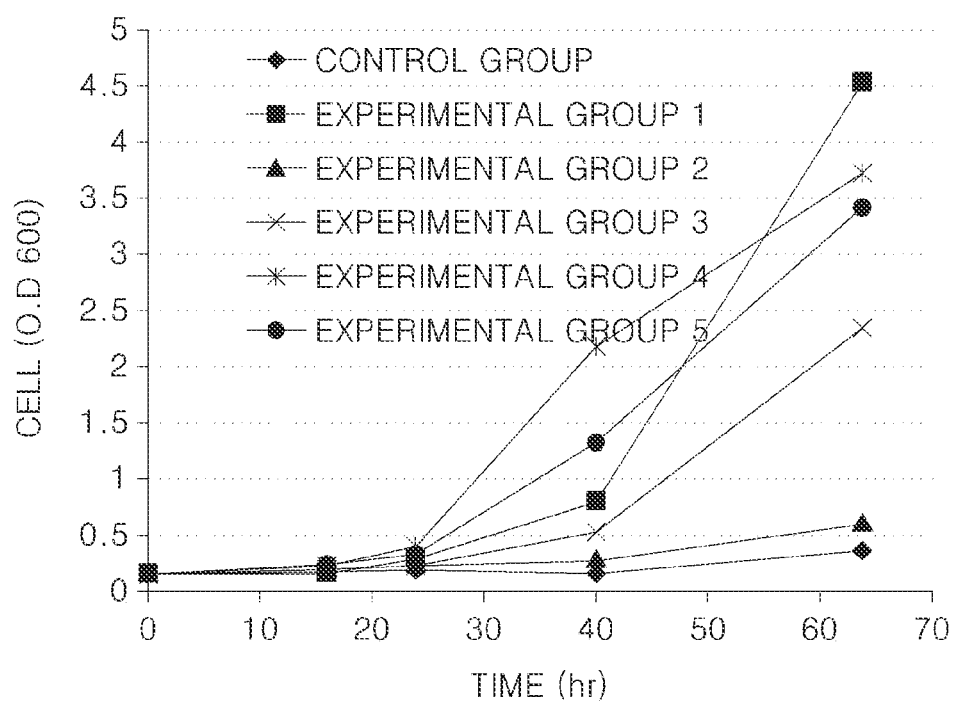
FIG. 4 is a graph displaying cell growth of 5 selected strains of lactic acid resistant yeast cells compared to a control.

FIG. 4 is a graph showing cell growth of 5 selected strains of lactic acid resistant yeast cells and control group cells. As shown in FIG. 4, 5 types of variant strains having excellent cell growth compared to the control group were obtained. 5 types of the variant strains showed a cell growth rate that is about 1.6 times to about 12.5 times as great as the cell growth rate of the control group.

Example 5

Analysis of Yield of Selected Lactic Acid Resistant Yeast Cells

The 5 types of strains selected in Example 3 were cultured under an anaerobic condition for about 48 hours. Culturing conditions were as follows: In a 250 ml flask, 50 ml of a lactic acid medium (pH 3.2) including 5.5% glucose, 4% lactic acid, 1% yeast extract, and 2% Bacto-peptone were cultured under an anaerobic condition at a speed of 230 rpm and at a temperature of 30° C. The OD value of initial cells was about 0.5. As a control group, *Saccharomyces cerevisiae* CEN.PK2-1D (Δ pdc1::ldh Δ cyb2::ldh Δ gpd1::ldh) cells were used.

Figure 5:
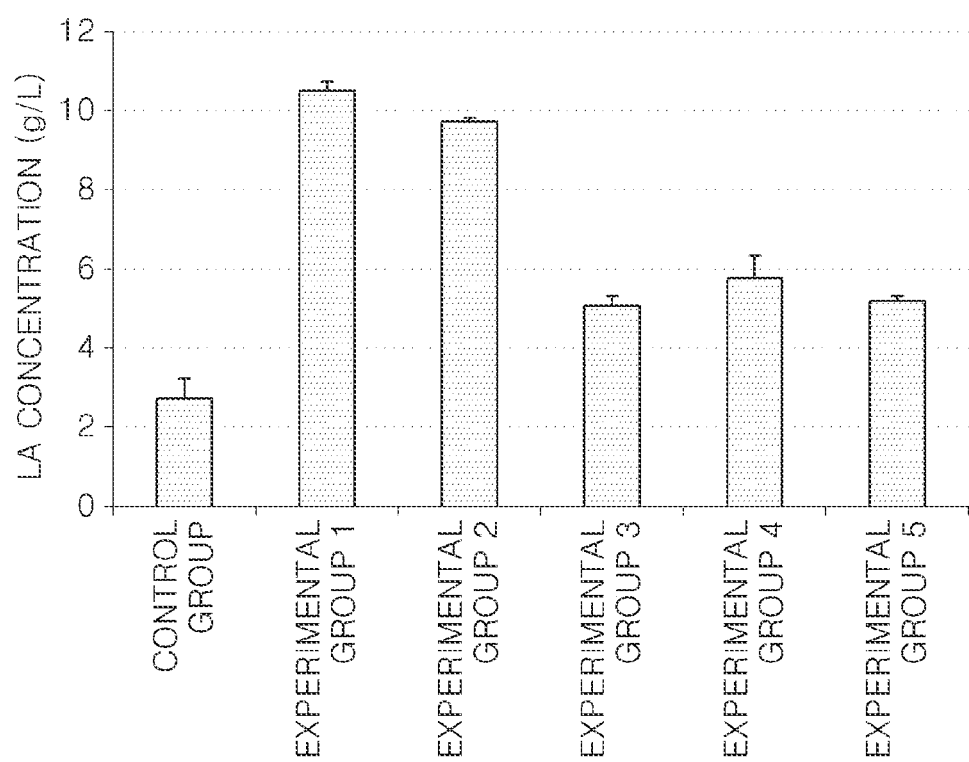
FIG. 5 is a graph displaying the lactic acid yield of 5 selected strains of lactic acid resistant yeast cells compared to control group cells.

FIG. 5 is a graph showing lactic acid yield of 5 selected strains of lactic acid resistant yeast cells and control group cells. As shown in FIG. 5 and Table 1, 5 types of variant strains having excellent lactic acid production compared to the control group were obtained. The 5 types of variant strains have amounts of lactic acid production that are about 1.9 times to about 3.8 times as great as that of the control group and yield rate of lactic acid that is about 1.4 times to about 13.4 times as great as that of the control group.

TABLE 1

| Strain | O.D | Amount of sugar consumption (g/L) | Lactic acid (g/L) | Lactic acid yield rate (%, g/g) |
|---|---|---|---|---|
| Control group | 7.8 ± 0.1 | 31 ± 2.4 | 2.8 ± 0.5 | 9.03 |
| Experimental group 1 | 9.7 ± 0 | 55 ± 0 | 11 ± 0.2 | 20.00 |
| Experimental group 2 | 9.7 ± 0.3 | 54 ± 1.2 | 9.8 ± 0 | 18.15 |
| Experimental group 3 | 7.6 ± 0.5 | 38 ± 1.7 | 5.1 ± 0.2 | 13.42 |
| Experimental group 4 | 8.4 ± 0.2 | 44 ± 1 | 5.8 ± 0.5 | 13.18 |
| Experimental group 5 | 9.1 ± 0 | 43 ± 0.6 | 5.2 ± 0.1 | 12.93 |

The mutant strain of *Saccharomyces cerevisiae* CEN.PK2-1D prepared in Experimental group 1 among Experimental groups 1 to 5 in Examples 4 and 5 was deposited in Korean Collection for Type Culture (KCTC) on Dec. 16, 2013 and received an accession number of KCTC 12532BP.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically modified *Saccharomyces cerevisiae* cell that produces lactate and has increased resistance to an acid having a pH range of 2.0 to 5.0 compared to a wild-type *Saccharomyces cerevisiae* cell, wherein the genetically modified *Saccharomyces cerevisiae* cell is the strain deposited under accession number Korean Collector for Type Culture (KCTC) 12532BP.

2. The genetically modified *Saccharomyces cerevisiae* cell according to claim 1, wherein the genetically modified *Saccharomyces cerevisiae* cell has increased lactate production capacity compared to the wild-type *Saccharomyces cerevisiae*.

3. A method of producing lactate, the method comprising:
    culturing the genetically modified *Saccharomyces cerevisiae* cell according to claim 1 in a culture medium to produce lactate; and
    retrieving the lactate from the culture medium.

4. The method of producing lactate according to claim 3, wherein the genetically modified *Saccharomyces cerevisiae* cell has increased lactate production capacity compared to a wild-type *Saccharomyces cerevisiae*.

* * * * *